(12) United States Patent
Odorzynski et al.

(10) Patent No.: US 7,491,863 B2
(45) Date of Patent: Feb. 17, 2009

(54) SECONDARY LOTIONED ARTICLE

(75) Inventors: Thomas W. Odorzynski, Green Bay, WI (US); Linda K. Lemerande, Waupaca, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 115 days.

(21) Appl. No.: 10/335,556

(22) Filed: Dec. 31, 2002

(65) Prior Publication Data

US 2004/0127877 A1   Jul. 1, 2004

(51) Int. Cl.
*A61F 13/15* (2006.01)
*A61L 9/00* (2006.01)
*A61L 9/04* (2006.01)

(52) U.S. Cl. .................. 604/359; 604/360; 604/367; 424/76.1; 424/76.4

(58) Field of Classification Search ................. 604/367, 604/361, 360, 359; 424/76.1–76.4; 442/97; 600/306, 345, 350
See application file for complete search history.

(56) References Cited

U.S. PATENT DOCUMENTS

| | | | |
|---|---|---|---|
| 2,450,059 A | 9/1948 | Rickerson | |
| 2,450,789 A | 10/1948 | Frieman | |
| 2,538,758 A | 1/1951 | Bricmont | |
| 2,688,328 A | 9/1954 | Marcus | |
| 3,276,944 A | 10/1966 | Levy | |
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,654,929 A | 4/1972 | Nilsson et al. | |
| 3,692,618 A | 9/1972 | Dorschner et al. | |
| 3,716,430 A | * 2/1973 | Croon et al. | 156/62.4 |
| 3,802,817 A | 4/1974 | Matsuki et al. | |
| 3,886,941 A | 6/1975 | Duane et al. | |
| 3,926,189 A | 12/1975 | Taylor | |
| 4,019,517 A | 4/1977 | Glassman | |
| 4,022,210 A | 5/1977 | Glassman | |
| 4,072,150 A | 2/1978 | Glassman | |
| 4,244,368 A | 1/1981 | Caradonna | |
| 4,265,245 A | 5/1981 | Glassman | |
| 4,340,563 A | 7/1982 | Appel et al. | |
| 4,496,360 A | 1/1985 | Joffe et al. | |

(Continued)

FOREIGN PATENT DOCUMENTS

CA   803714   1/1969

(Continued)

OTHER PUBLICATIONS

Abstract for DE 29819087U1, Mar. 9, 2000, Schulz K.

*Primary Examiner*—Jacqueline F. Stephens
(74) *Attorney, Agent, or Firm*—Richard M. Shane

(57) ABSTRACT

A disposable secondary article includes a liquid-permeable substrate that has a garment-facing surface and a body-facing surface. A lotion is applied to the body-facing surface of the liquid-permeable substrate. The secondary article optionally includes an attachment means for attaching the secondary absorbent article to a primary absorbent article. Additionally, the secondary article optionally includes a cover to protect the lotion until just prior to use. The secondary article provides a caregiver or wearer an alternative to applying lotions by hand.

12 Claims, 3 Drawing Sheets

U.S. PATENT DOCUMENTS

| | | | |
|---|---|---|---|
| 4,560,372 | A | 12/1985 | Pieniak |
| 4,578,073 | A | 3/1986 | Dysart et al. |
| 4,597,760 | A | 7/1986 | Buell |
| 4,597,761 | A | 7/1986 | Buell |
| 4,623,339 | A | 11/1986 | Ciraldo et al. |
| 4,790,836 | A * | 12/1988 | Brecher ................. 604/359 |
| 4,834,737 | A | 5/1989 | Khan |
| 4,938,756 | A | 7/1990 | Salek |
| 4,968,312 | A | 11/1990 | Khan |
| 5,108,385 | A | 4/1992 | Snyder |
| 5,176,672 | A | 1/1993 | Bruemmer et al. |
| 5,192,606 | A | 3/1993 | Proxmire et al. |
| 5,236,428 | A | 8/1993 | Zajackowski |
| 5,397,319 | A | 3/1995 | Suzuki et al. |
| 5,401,266 | A | 3/1995 | Runeman et al. |
| 5,405,342 | A | 4/1995 | Roessler et al. |
| 5,613,959 | A | 3/1997 | Roessler et al. |
| 5,731,062 | A | 3/1998 | Kim et al. |
| 5,782,819 | A | 7/1998 | Tanzer et al. |
| 5,853,402 | A | 12/1998 | Faulks et al. |
| 5,879,341 | A | 3/1999 | Odorzynski et al. |
| 5,925,026 | A | 7/1999 | Arteman et al. |
| 6,118,041 | A | 9/2000 | Roe et al. |
| 6,120,783 | A | 9/2000 | Roe et al. |
| 6,149,934 | A | 11/2000 | Krzysik et al. |
| 6,153,209 | A | 11/2000 | Vega et al. |
| 6,229,061 | B1 | 5/2001 | Dragoo et al. |
| 6,287,581 | B1 | 9/2001 | Krzysik et al. |
| 6,296,862 | B1 | 10/2001 | Paul et al. |
| 6,436,079 | B1 | 8/2002 | Blenke et al. |
| D462,439 | S | 9/2002 | Montgomery et al. |
| D463,022 | S | 9/2002 | Montgomery et al. |
| 6,692,475 | B2 | 2/2004 | Mishima |
| 6,756,520 | B1 * | 6/2004 | Krzysik et al. ............. 604/360 |
| 2002/0115968 | A1 | 8/2002 | Lin |
| 2002/0143316 | A1 | 10/2002 | Sherrod et al. |

FOREIGN PATENT DOCUMENTS

| | | |
|---|---|---|
| DE | 29819087 U1 | 3/2000 |
| EP | 0319314 A2 | 6/1989 |
| EP | 0549988 B1 | 7/1993 |
| EP | 0945110 | 9/1999 |
| EP | 1120 097 * | 1/2001 |
| EP | 0814739 | 5/2002 |
| GB | 2 269 999 A | 3/1994 |
| WO | WO 89/11842 | 12/1989 |
| WO | WO 91/10413 | 7/1991 |
| WO | WO 91/16871 | 11/1991 |
| WO | WO 96/32912 | 10/1996 |
| WO | WO 00/00145 | 1/2000 |
| WO | WO 00/69481 | 11/2000 |
| WO | WO 01/83876 A1 | 11/2001 |
| WO | WO 02/080834 | 10/2002 |
| WO | WO 03/034965 A2 | 5/2003 |

* cited by examiner

SECONDARY LOTIONED ARTICLE

BACKGROUND OF THE INVENTION

The present invention generally relates to disposable secondary articles useful for bolstering the effectiveness of primary absorbent articles. More particularly, the present invention relates to disposable secondary articles useful when there is a need to provide a lotioned surface on the bodyside surface of a disposable primary absorbent article such as a disposable diaper.

Disposable diapers and incontinence products are designed to absorb bodily fluids such as urine and watery feces. Skin wellness is generally maintained by absorbent products which absorb bodily fluids and present a dry surface to the skin of the wearer. However, there are times when the skin covered by an absorbent product can become red, irritated, and sore. During these times, skin wellness can be enhanced by contacting the skin with lotion designed to protect the skin from further harm and to promote healing of the skin.

The application of moderate amounts of lotion to the bodyside liner of a primary absorbent article is known in the art. However, some caregivers prefer to apply large quantities of lotion to irritated skin. While a caregiver could apply the desired quantity of lotion to the primary absorbent article or the skin of the wearer, the application process can be exceedingly messy, resulting in lotion all over the fingers and hands of the caregiver. It is impractical for the manufacturer to apply large quantities of lotion to the body-side liner of packaged primary absorbent articles for several reasons. First, many caregivers do not want to use large quantities of lotion. Applying the lotion to the packaged articles would leave the caregiver no choice whether or not to use the lotion. Second, large quantities of lotion applied to the body-side liner of primary absorbent articles tend to migrate into the absorbent core of the primary absorbent article when packaged. Therefore, there is a need for a lotioned secondary article that can be purchased separately, that can be used only when needed, and that can be positioned within a primary absorbent article while maintaining the lotion on the body-side surface of the primary absorbent article.

SUMMARY OF THE INVENTION

The aforementioned needs for a disposable secondary article to be used in conjunction with a primary absorbent article are addressed by the present invention which provides a disposable secondary article. In one aspect of the present invention, the disposable secondary article includes a liquid-permeable substrate that has a garment-facing surface and a body-facing surface. A lotion is applied to the body-facing surface of the liquid-permeable substrate. In one aspect of the invention, the substrate is substantially nonabsorbent.

The lotion desirably includes one or more of the following ingredients: emollients, waxes, viscosity enhancers, active ingredients, and so forth. Desirable, the lotion has a semisolid consistency. In one aspect of the invention, the lotion is arranged in multiple stripes on the body-facing surface of the substrate. In one embodiment, the lotion is applied to at least about 5 percent of the body-facing surface of the substrate. In another embodiment, the lotion has a basis weight on the surface of the substrate of greater than about 1 mg/cm$^2$. In even another embodiment, the basis weight of the lotion is greater than the basis weight of the substrate.

In a further aspect of the invention, the disposable secondary article includes an attachment means attached to the garment-facing surface of the substrate. Examples of suitable attachment means include, but are not limited to garment adhesives, hook materials, loop materials, roughened surfaces, and so forth. The attachment means may further include a removable peel strip.

In a further aspect of the invention, the disposable secondary article includes a cover releasably adhered to the lotion. Examples of suitable covers include, but are not limited to coated papers, films, and so forth. Desirably, the cover has a Drape Stiffness bending length of between about 0.25 centimeters and about 12 centimeters.

In another aspect, the present invention includes an absorbent system that includes a primary absorbent article to which is attached a secondary article. The secondary article includes a liquid-permeable substrate having a garment-facing surface and a body-facing surface, an attachment means attached to the garment-facing surface, and a lotion applied to the body-facing surface. The attachment means attaches the secondary article to the primary absorbent article. In one embodiment, the secondary article includes a cover releasably adhered to the lotion. In another embodiment, the secondary article is substantially the same shape as the primary absorbent article.

Other features and aspects of the present invention are discussed in greater detail below.

BRIEF DESCRIPTIONS OF THE DRAWINGS

DETAILED DESCRIPTION

The invention will now be described in detail with reference to particular embodiments thereof. The embodiments are provided by way of explanation of the invention, and not meant as a limitation of the invention. For example, features described or illustrated as part of one embodiment may be used with another embodiment to yield still a further embodiment. It is intended that the present invention include these and other modifications and variations as come within the scope and spirit of the invention.

As used herein and in the claims, the term "comprising" is inclusive or open-ended and does not exclude additional unrecited elements, compositional components, or method steps. Accordingly, the term "comprising" encompasses the more restrictive terms "consisting essentially of" and "consisting of."

The present invention provides a disposable secondary article that includes a substrate, an optional attachment means, a lotion, and an optional cover. The disposable secondary article is sized to fit within the target zone of a primary absorbent article. As used herein, the term "disposable" refers to articles which are intended to be discarded after a limited use and that are not intended to be laundered or otherwise restored for reuse.

Figure 1:
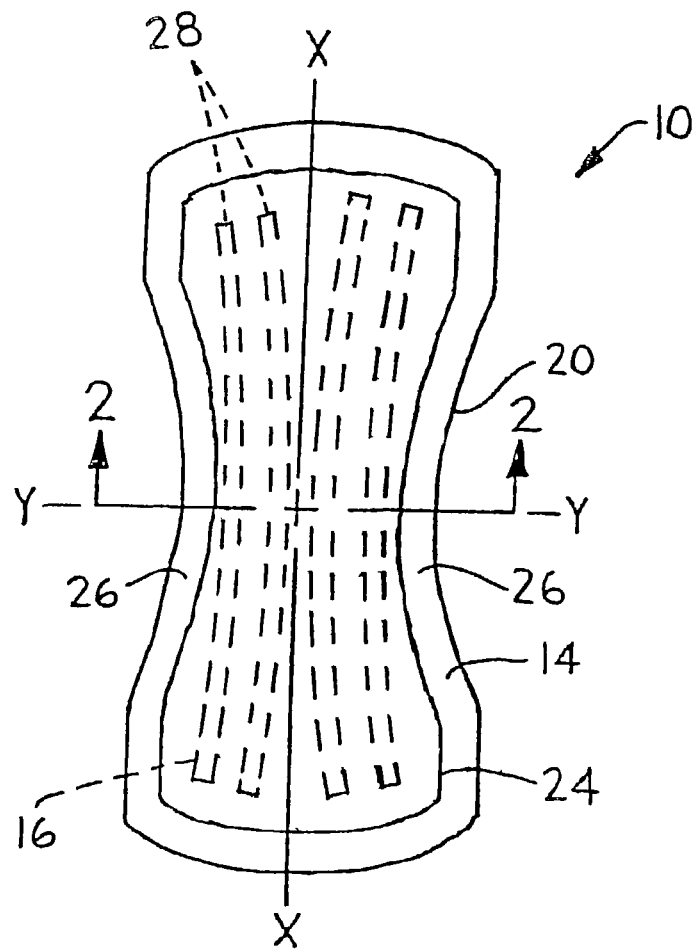
FIG. 1 is a top view of a disposable secondary lotioned article.
Figure 2:
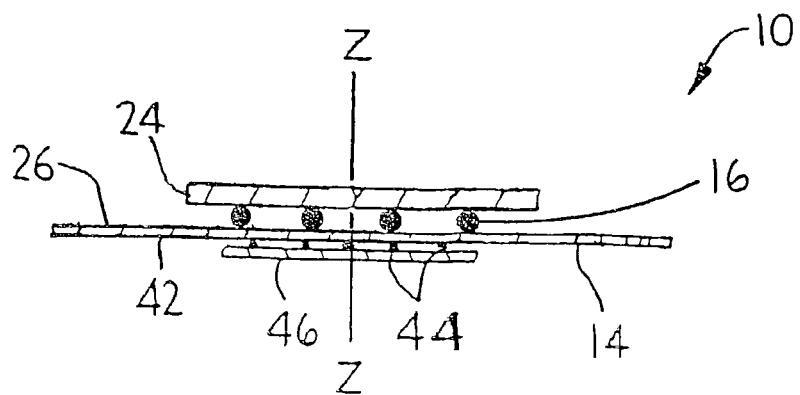
FIG. 2 is a cross-sectional view of the secondary article shown in FIG. 1 taken along line 2-2.
Figure 3:
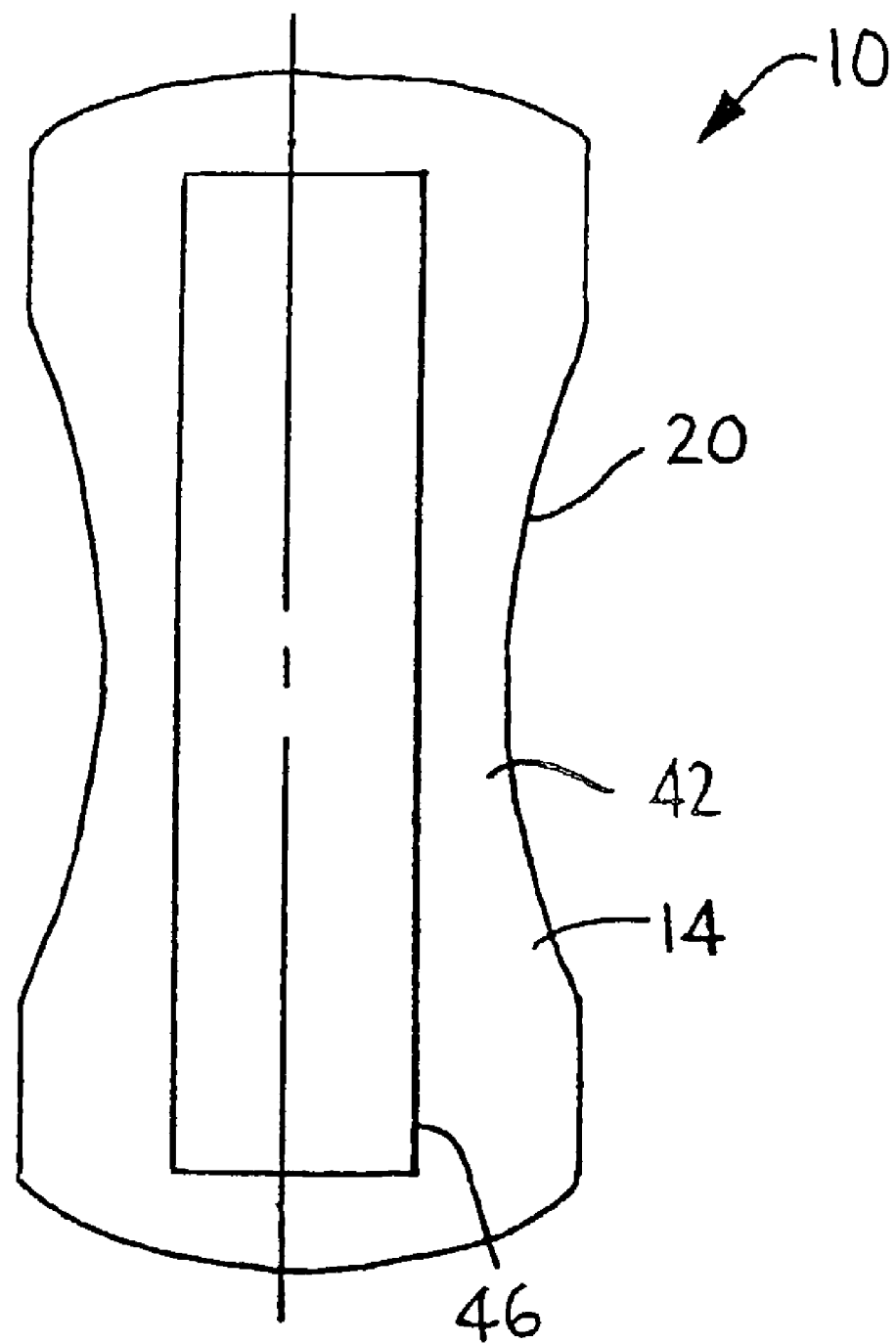
FIG. 3 is a bottom view of the secondary article shown in FIG. 1.

Referring to FIGS. 1-3, a secondary article 10 is shown constructed of a substrate 14, an optional attachment means 44, lotion 16, and an optional cover 24. The lotion 16 is applied to the substrate 14 and optionally covered by the cover 24 to form the secondary article 10 having a crotch portion 20. The secondary article 10 is an elongated member having a longitudinal axis x-x, a transverse axis y- y and a vertical axis z- z. The secondary article 10 can have a rectangular, hourglass, race track, oval, elliptical or other geometrical configuration when viewed from the top. The secondary article 10 has an overall length measured parallel to the longitudinal axis x-x. In some embodiments, the secondary article 10 has an overall length of less than about 600 millimeters (mm). In other embodiments, the secondary article 10 may have an overall length of less than about 500 mm, less than about 400 mm, less than about 300 mm, or less than about 200 mm. The secondary article 10 also has a crotch width measured parallel to the transverse axis y-y. In some embodiments, the secondary article 10 has a crotch width of less than about 200 mm. In other embodiments, the crotch width of the secondary article 10 may be less than about 175 mm, less than about 150 mm, less than about 125 mm, less than about 100 mm, or less than about 75 mm. It should be noted that the secondary article 10 could have a wider width when measured away from the crotch portion. The secondary article 10 also has an overall height measured parallel to the vertical axis z-z. In some embodiments, the secondary article 10 has an overall height of from about 2 mm to about 12 mm. In other embodiments, the height of the secondary article 10 may be less than about 10 mm or less than about 8 mm. Desirably, the secondary article 10 is sized to fit within a primary absorbent article. All of the above length, width, and height dimensions are measured with respect to the substrate 14.

The substrate 14 suitably presents a body-facing surface 26 that is compliant, soft feeling, and nonirritating to the skin of the wearer. The substrate 14 can be constructed from natural or synthetic material. The substrate 14 can be formed from a woven material, nonwoven material, finely perforated film, net material, porous foams, reticulated foams, and so forth. Suitable materials include, but are not limited to, fibrous materials such as bonded carded webs, meltblown fabrics, and spunbond fabrics. Suitable fibers include, but are not limited to, polyester, polypropylene, polyethylene, nylon or other heat-bondable fibers. Other polyolefins, such as copolymers of polypropylene and polyethylene, and linear low-density polyethylene also work well. As an example, spunbond material may be used as the substrate 14. Spunbond material is a nonwoven material formed, for example, from polypropylene fibers. Spunbond fabric is sold commercially by Kimberly-Clark Corporation having an office at 401 North Lake Street, Neenah, Wis. 54956. The spunbond material can contain from about 1% to about 2% titanium dioxide pigment to give it a clean, white appearance. The production of spunbonded nonwoven webs is illustrated in patents such as Appel, et al., U.S. Pat. No. 4,340,563, Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; Matsuki et al., U.S. Pat. No. 3,802,817; and Harmon, Canadian Patent Number 803,714, the entire contents of these patents being incorporated herein by reference.

Another example of a material useful as the substrate 14 includes three-dimensional fiber networks made from textile fabrics that have projections and optional depressions which are compressible and return substantially to their original shape after being depressed. Materials of this type are described, for example, in Kim et al., U.S. Pat. No. 5,731,062, the entire contents of this patent being incorporated herein by reference. Such material is a synthetic thermoplastic fiber network in flexible sheets having projections and/or indentations for use as cushions and/or impact-absorbing components. These fiber networks are typically made by thermo-mechanical deformation of textile fabrics that are made from thermoplastic fibers.

The substrate 14 can be formed from materials having a range of basis weights. As an example, when the substrate 14 is formed from spunbond material, the material may have a basis weight of from about 10 grams per square meter (gsm) to about 34 gsm. As another example, the basis weight of the spunbond material may be from about 12 gsm to about 17 gsm.

The substrate 14 is liquid and vapor permeable. By "liquid and vapor permeable" it is meant that body fluids, especially urine, and vapors can pass therethrough. The substrate 14 is designed to allow body fluid, particularly urine, to quickly pass therethrough and be received by a primary absorbent article 22, see FIG. 4. The substrate 14 is suitably employed to help isolate the skin of the wearer from liquids held in the primary absorbent article 22. Because the substrate 14 is to be placed in contact with the genital area of a human body, the substrate 14 is capable of passing body fluid, voluntarily or involuntarily expelled from the urethra, downwardly into the primary absorbent article 22. The substrate 14 can be constructed with pores or openings that permit liquids and gases to pass therethrough. Additionally, the material from which the substrate 14 is constructed can be treated to be hydrophilic. The substrate 14 is desirably less hydrophilic than the primary absorbent article 22 to present a relatively dry surface against the skin of the wearer, and is desirably sufficiently porous to be liquid and vapor permeable, permitting bodily fluids to readily penetrate through its thickness. A suitable treatment includes, but is not limited to, treatment with a surfactant commercially available from Uniqema Inc., a division of ICI of New Castle, Del., U.S.A., under the trade designation AHCOVEL Base N-62. The surfactant may be applied by any conventional means, such as spraying, printing, brush coating or the like. The surfactant may be applied to the entire substrate 14 or may be selectively applied to particular sections of the substrate 14, such as the medial section along the longitudinal axis x-x of the secondary article 10, to provide greater wettability of such sections.

While the substrate 14 may be liquid and vapor permeable, porous, or hydrophilic, the substrate 14 is desirably substantially nonabsorbent to present a drier body-facing surface 26 to the skin of the wearer. By nonabsorbent it is meant that liquids are not permanently retained with the substrate 14, but rather pass through the substrate 14 without remaining therein.

The secondary article 10 of the present invention further includes the lotion 16 on the body-facing surface 26 of the substrate 14. As used herein, the term "lotion" may include any of a variety of creams, ointments, salves, medicinal products, and so forth known by those skilled in the art to promote skin wellness. The lotion 16 desirably includes one or more of the following: emollients, waxes, viscosity enhancers, and other active ingredients. For example, the lotion 16 may include from about 5 to about 95 weight percent of an emollient, from about 5 to about 50 weight percent of a wax, and from about 1 to about 25 weight percent of a viscosity enhancer based on a total weight of the lotion 16. The lotion 16 may include other ingredients as well.

Emollients in the lotion 16 act as lubricants to reduce the abrasiveness of the substrate 14 to the skin and, upon transfer to the skin, help to maintain the soft, smooth and pliable appearance of the skin. Suitable emollients which can be incorporated into the lotion 16 include oils such as petroleum based oils, vegetable based oils, mineral oils, natural or synthetic oils, silicone oils, lanolin and lanolin derivatives, kaolin and kaolin derivatives and the like and mixtures thereof; esters such as cetyl palmitate, stearyl palmitate, cetyl stearate, isopropyl laurate, isopropyl myristate, isopropyl palmitate and the like and mixtures thereof; glycerol esters; ethers such as eucalyptol, cetearyl glucoside, dimethyl isosorbicide polyglyceryl-3 cetyl ether, polyglyceryl-3 decyltetradecanol, propylene glycol myristyl ether and the like and mixtures thereof; alkoxylated carboxylic acids; alkoxylated alcohols; fatty alcohols such as octyidodecanol, lauryl, myristyl, cetyl, stearyl and behenyl alcohol and the like and mixtures thereof; and the like and mixtures thereof. For example, a particularly well suited emollient is petrolatum. Other conventional emollients may also be added in a manner which maintains the desired properties of the lotion 16.

The lotion 16 may desirably include from about 5 to about 95 weight percent, more desirably from about 20 to about 90 weight percent, and even more desirably from about 40 to about 85 weight percent of the emollient. Lotion formulations which include an amount of emollient greater than the recited amounts tend to have lower viscosities which undesirably lead to migration of the lotion 16. Lotion formulations which include an amount of emollient less than the recited amounts tend to provide less transfer to the skin of the wearer.

Waxes are optionally provided in the lotion 16 as immobilizing agents for the emollient and any other active ingredient. Wax may be used to provide a more semisolid consistency to the lotion 16 to help prevent undesirable migration of the lotion. The wax may further function as an emollient, occlusive agent, moisturizer, barrier enhancer and combinations thereof.

Suitable waxes which can be incorporated into the lotion 16 include animal, vegetable, mineral or silicone based waxes which may be natural or synthetic such as, for example, bayberry wax, beeswax, C30 alkyl dimethicone, candelilla wax, carnauba, ceresin, cetyl esters, esparto, hydrogenated cottonseed oil, hydrogenated jojoba oil, hydrogenated jojoba wax, hydrogenated microcrystalline wax, hydrogenated rice bran wax, japan wax, jojoba buffer, jojoba esters, jojoba wax, lanolin wax, microcrystalline wax, mink wax, motan acid wax, motan wax, ouricury wax, ozokerite, paraffin, PEG-6 beeswax, PEG-8 beeswax, rezowax, rice bran wax, shellac wax, spent grain wax, spermaceti wax, steryl dimethicone, synthetic beeswax, synthetic candelilla wax, synthetic carnuba wax, synthetic japan wax, synthetic jojoba wax, synthetic wax, and the like and mixtures thereof.

The lotion 16 may include from about 5 to about 50 weight percent, desirably from about 10 to about 40 weight percent, and more desirably from about 15 to about 30 weight percent of the wax. Lotion formulations which include an amount of wax less than the recited amounts tend to have lower viscosities which undesirably lead to migration of the lotion. Lotion formulations which include an amount of wax greater than the recited amounts tend to provide less transfer to the skin of the wearer.

A viscosity enhancer may be added to the lotion 16 to increase the viscosity to help stabilize the formulation on the body-facing surface 26 of the substrate 14 and thereby reduce migration of the lotion 16. Suitable viscosity enhancers which can be incorporated into the lotion 16 include polyolefin resins, lipophilic/oil thickeners, ethylene/vinyl acetate copolymers, polyethylene, silica, talc, colloidal silicone dioxide, zinc stearate, cetyl hydroxy ethyl cellulose and other modified celluloses and the like and mixtures thereof. The lotion 16 may include from about 0.1 to about 25 weight percent of the viscosity enhancer for reduced migration of the lotion 16.

If it is desired that the lotion 16 treat the skin, it can also include an active ingredient such as a diaper rash skin protectant. Skin protectants are drug products which protect injured or exposed skin or mucous membrane surface from harmful or annoying stimuli. Suitable active ingredients, in addition to those mentioned above as suitable emollients, which can be incorporated into the lotion 16 include, but are not limited to, alantoin and its derivatives, aluminum hydroxide gel, calamine, cocoa butter, dimethicone, cod liver oil, glycerin, kaolin and its derivatives, lanolin and its derivatives, mineral oil, shark liver oil, talc, topical starch, zinc acetate, zinc carbonate, and zinc oxide and the like, and mixtures thereof. The lotion 16 may include from about 0.10 to about 95 weight percent of the active ingredient depending upon the skin protectant and the amount desired to be transferred to the skin.

In order to better enhance the benefits to the wearer, additional ingredients can be included in the lotion 16. For example, the classes of ingredients that may be used and their corresponding benefits include, without limitation: antifoaming agents (reduce the tendency of foaming during processing); antimicrobial actives; antifungal actives; antiseptic actives; antioxidants (product integrity); astringents—cosmetic (induce a tightening or tingling sensation on skin); astringent—drug (a drug product which checks oozing, discharge, or bleeding when applied to skin or mucous membrane and works by coagulating protein); biological additives (enhance the performance or consumer appeal of the product); colorants (impart color to the product); deodorants (reduce or eliminate unpleasant odor and protect against the formation of malodor on body surfaces); other emollients (help to maintain the soft, smooth, and pliable appearance of the skin by their ability to remain on the skin surface or in the stratum corneum to act as lubricants, to reduce flaking, and to improve the skin's appearance); external analgesics (a topically applied drug that has a topical analgesic, anesthetic, or antipruritic effect by depressing cutaneous sensory receptors, or that has a topical counterirritant effect by stimulating cutaneous sensory receptors); film formers (to hold active ingredients on the skin by producing a continuous film on skin upon drying); fragrances (consumer appeal), silicones/organomodified silicones (protection, tissue water resistance, lubricity, tissue softness), oils (mineral, vegetable, and animal); natural moisturizing agents (NMF) and other skin moisturizing ingredients known in the art; opacifiers (reduce the clarity or transparent appearance of the product); powders (enhance lubricity, oil adsorption, provide skin protection, astringency, opacity, etc.); skin conditioning agents; solvents (liquids employed to dissolve components found useful in the cosmetics or drugs); and surfactants (as cleansing agents, emulsifying agents, solubilizing agents, and suspending agents).

The lotion 16 desirably has a semisolid consistency at ambient temperatures so as to minimize the migration of the lotion 16 away from the substrate 14. The lotion 16 of the present invention desirably has a viscosity of from about 50 to about 10000 centipoise, more desirably from about 100 centipoise to about 500 centipoise, and even more desirably from about 150 to about 250 centipoise at body temperature. Lotion formulations which have lower viscosities at body temperature exhibit undesirable migration of the lotion through the substrate 14 and into the absorbent core 62 of the primary absorbent article 22 which can undesirably result in reduced transfer to the skin. Lotion formulations which have higher viscosities at body temperature may be so solid as to inhibit transfer of the lotion 16 to the skin.

As representatively illustrated in FIG. 1, the body-facing surface 26 of the substrate 14 may include multiple stripes 28 of the lotion 16 applied thereto. For example, the body-facing surface 26 of the substrate 14 may include from 1 to 10 stripes 28 of lotion 16 extending generally in the direction of the longitudinal axis x-x of the secondary article 10. The stripes 28 may extend the full length of the substrate 14 or only a portion thereof. The stripes 28 may define a width of from about 0.2 centimeters to about 1 centimeter. The lotion 16 may also be applied to the substrate 14 in other patterns including, but not limited to, dots, piles, swirls, and so forth. Alternatively, the lotion 16 may be applied to the entire body-facing surface 26 of the substrate 14 or may be selectively applied to particular sections of the body-facing surface 26, such as the medial section along the longitudinal axis x-x of the secondary article 10, to provide greater lubricity of such sections and to transfer such lotion to the skin of the wearer.

The lotion 16 should cover a sufficient amount of the surface area of the substrate 14 to ensure adequate transfer to the skin and reduced abrasion between the substrate 14 and the skin of the wearer. Desirably, the lotion 16 is applied to at least about 5 percent and more desirably at least about 25 percent of the body-facing surface 26 of the substrate 14.

The lotion 16 can be applied to the substrate 14 at any add-on level which provides the desired benefits. In some embodiments, the total add-on level of the lotion 16 is greater than about 1 mg/cm$^2$, greater than about 3 mg/cm$^2$, or greater than about 5 mg/cm$^2$. In other embodiments, the total add-on level of the lotion 16 may be from about 1 to about 100 mg/cm$^2$, from about 3 to about 50 mg/cm$^2$, or from about 5 to about 40 mg/cm$^2$. In one embodiment, the total weight of the lotion 16 is greater than the total weight of the substrate 14. In another embodiment, the total weight of the lotion 16 is greater than twice the total weight of the substrate 14. The add-on amount will depend upon the desired effect of the lotion 16 on the product attributes and the specific lotion formulation.

The lotion 16 may be applied to the substrate 14 in any of many ways known to those skilled in the art. A preferred method to uniformly apply the lotion 16 to the surface of the substrate 14 is spraying or slot coating, because it is the most exact process and offers maximum control of the formulation distribution and transfer rate. However, other methods, such as rotogravure, inkjet, or flexographic printing, can be used.

As another example, the lotion 16 may be applied to the substrate 14 by (a) heating the lotion formulation to reduce the viscosity of the formulation, (b) uniformly applying the formulation to the body-facing surface 26 of the substrate 14; and (c) cooling the deposits of the formulation. Desirably, cooling of the deposits occurs almost instantaneously, without the need for external cooling means such as chill rolls. This can occur if the lotion formulation is heated to a temperature only slightly above ambient temperature. However, external means such as chill rolls, either before or after the application of lotion 16, can be used if desired to accelerate cooling of the formulation.

The secondary article 10 of the present invention optionally includes the cover 24. The optional cover 24 is designed to protect the lotion 16 prior to the exposure of the lotion 16 by removal of the cover 24. The cover 24 is designed to be removed by the consumer after the secondary article 10 is positioned within the primary absorbent article 22, thereby exposing the lotion 16 just prior to positioning and attaching the primary absorbent article 22 around the wearer.

The optional cover 24 can be a releasable or removable peel strip. For example, the cover 24 can be a white Kraft paper, coated on one side so that it can be easily released from the lotion 16. Alternatively, the cover 24 can be a film that will adhere to the lotion 16, yet can be easily released from the lotion 16 by the consumer when it is time to remove the cover 24. The cover 24 is generally slightly larger in overall dimensions when compared to the lotion 16 so as to fully protect the lotion 16 from contamination. The cover 24 can be formed from materials having a range of basis weights. The material should have a basis weight of from about 10 gsm to about 50 gsm. Desirably, the basis weight of the material is from about 12 gsm to about 40 gsm.

Desirably, the optional cover 24 provides lateral support to the secondary article 10 prior to use and during the process of positioning the secondary article 10 in the primary absorbent article 22. Lateral support minimizes the risk that the secondary article 10 will fold over on itself and allows the secondary article 10 to be positioned more easily within a primary absorbent article 22.

The "Drape Stiffness" test measures the resistance to bending of the cover. The bending length is a measure of the interaction between the cover weight and stiffness as shown by the way in which a cantilevered sample bends under its own weight. In this test, a sample is slid at 12 cm/min, in a direction parallel to its long dimension, so that its leading edge projects from the edge of a horizontal surface. The length of the overhang is measured when the tip of the sample falls under its own weight to the point where the line joining the tip to the edge of a platform makes a 41.50° angle with the horizontal. The longer the overhang, the more resistant the sample is to bending; thus, higher numbers indicate stiffer covers. This method conforms to specifications of ASTM Standard Test D 1388.

The test samples to determine bending length are cut into rectangular strips measuring about 3 cm wide and about 25 cm long. A suitable Drape-Flex Stiffness Tester, such as FRL-Cantilever Bending Tester, Model 79-10 available from Testing Machines Inc., located in Amityville, N.Y., may be used to perform the test. The bending length is calculated as one-half of the length of the overhang of the specimen when it reaches the 41.5° slope.

Desirably, the optional cover 24 has a bending length according to the Drape Stiffness test of between about 0.25 centimeters and about 12 centimeters, more desirably between about 0.5 centimeters and about 10 centimeters, more desirably between about 1 centimeter and about 8 centimeters, more desirably between about 2 centimeters and about 6 centimeters, and even more desirably between about 3 centimeters and about 5 centimeters.

Still referring to FIG. 2, the substrate 14 of the secondary article 10 has a garment-facing surface 42. Secured to the garment-facing surface 42 is an optional attachment means 44, the purpose of which is to allow attachment of the secondary article 10 to the primary article 22. In other embodiments, there may be more than one attachment means 44 attached to the garment-facing surface 42. Those skilled in the art will appreciate that more than one attachment means 44 may be positioned in any number of configurations that will provide adequate attachment of the secondary article 10 to the primary absorbent article 22. For example, there may be one attachment means attached to the garment-facing surface 42 at one end of the secondary article 10 and a second attachment means attached to the garment-facing surface 42 at the opposite end of the secondary article 10.

The optional attachment means 44 is desirably one or more strips of a garment adhesive. However, the attachment means 44 can include other forms of attachment mechanisms. Other forms of attachment mechanisms that can be utilized include hook and/or loop fasteners, tape, glue, etc. A VELCRO® fastener is one form of a hook fastener that engages a loop material. VELCRO® is a registered trademark of Velcro Industries having a mailing address of 406 Brown Avenue, Manchester, N. H. 03103. When the attachment means 44 is a garment adhesive, the adhesive can be either a hot or cold melt adhesive that is sprayed, brushed, slot coated or otherwise applied onto the garment-facing surface 42 of the substrate 14. The garment adhesive can be applied as one or more beads, lines or strips of adhesive aligned approximately parallel to the longitudinal axis x-x. Alternatively, the garment adhesive can be applied as one or more beads, lines or strips of adhesive aligned approximately perpendicular to the longitudinal axis x-x. Desirably, the garment adhesive is a hot melt adhesive. Garment adhesive is commercially available from several vendors. One such vendor is National Starch and Chemical Company having an office at 10 Finderne Avenue, Bridgewater, N.J. 08807.

When a hook and loop fastener is used as the optional attachment means 44, the hook portion can be secured to a portion of the substrate 14 and the loop portion can be secured to a portion of the primary absorbent article 22 or vice versa. It should also be noted that some materials, like spunbond material, can serve the same function as a loop material and therefore a separate patch of loop material does not have to be secured opposite to the hook material. For example, if a patch of hook material is secured to the substrate 14, the primary absorbent article 22 having a liner of spunbond material will not be required to have a patch of loop material secured to it.

As mentioned above, the substrate 14 has a garment-facing surface 42 and a portion of this garment-facing surface 42 will contact the primary absorbent article 22. The portion of the garment-facing surface 42 that will contact the primary absorbent article 22 can be formed to have a high coefficient of friction making it a non-skid surface. For example, the garment-facing surface 42 can consist of a roughened surface, a treated surface or be made from a non-skid material. The roughened, treated or non-skid surface will provide a physical attachment to the primary absorbent article 22. Another way of stating this is to say that the non-skid portion of the garment-facing surface 42 serves a similar function as the attachment means 44.

The optional attachment means 44 can be protected from contamination by a releasable or removable peel strip 46. The peel strip 46 is designed to be removed by the consumer just prior to positioning and attaching the secondary article 10 to the primary absorbent article 22. The releasable peel strip 46 is generally slightly larger in overall dimensions when compared to the attachment means 44 so as to enable the secondary article 10 to be manufactured at high speeds. By "high speeds" it is meant the ability to manufacture at a speed of more than 200 secondary articles per minute. The peel strip 46 can be a white Kraft paper, coated on one side so that it can be easily released from the attachment means 44.

In accordance with one embodiment of this invention, the secondary article 10 optionally may include a pair of containment flaps that are configured to provide a barrier to the lateral flow of body exudates. The containment flaps may be located along the laterally opposing side edges of the secondary article 10 adjacent the side edges of the substrate 14. Each containment flap typically defines an unattached edge that is configured to maintain an upright, perpendicular configuration in at least the crotch region of the secondary article 10 to form a seal against the body of the wearer. Each containment flap may extend longitudinally along at least a portion of a length of the substrate 14. Desirably, each containment flap extends along substantially the entire length of the substrate 14 to better contain the body exudates. Such containment flaps are generally well known to those skilled in the art. For example, suitable constructions and arrangements for containment flaps are described in Enloe, U.S. Pat. No. 4,704,116, the entire content of this patent being incorporated herein by reference.

Figure 4:
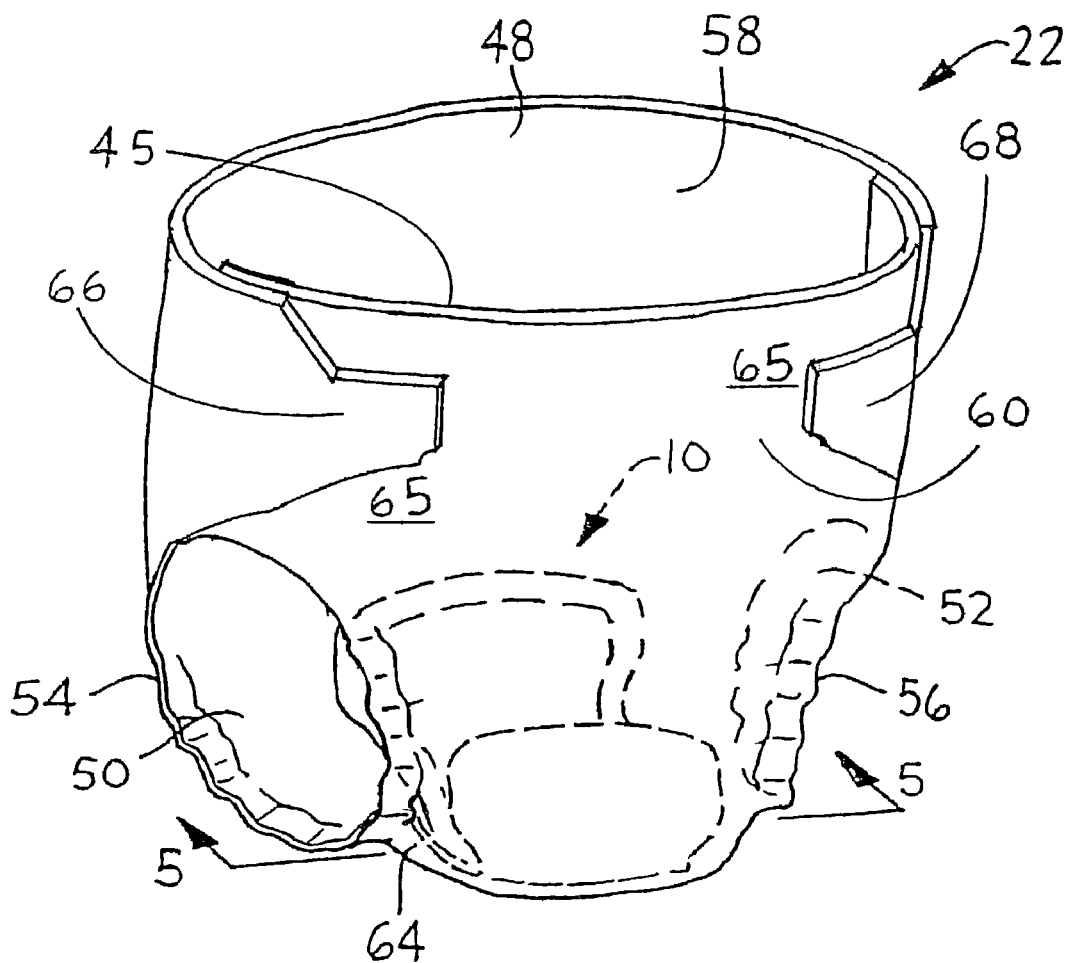
FIG. 4 is a perspective view of the secondary article shown in FIG. 1 positioned in the crotch portion of a primary absorbent article.
Figure 5:
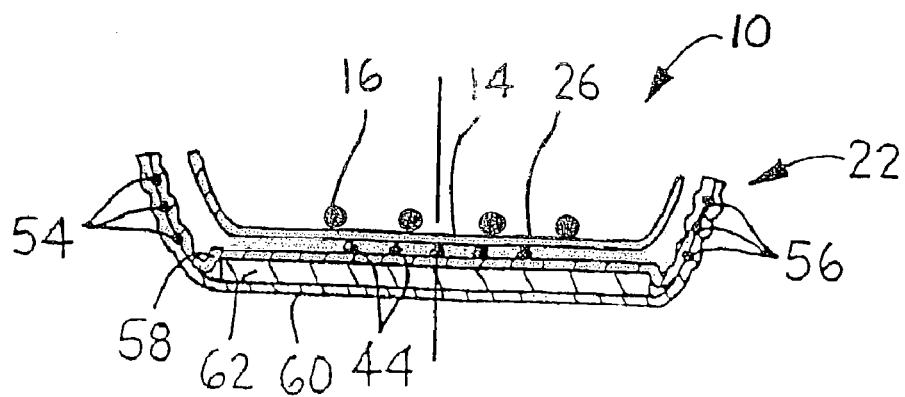
FIG. 5 is a cross-sectional view of the combination secondary article and primary absorbent article shown in FIG. 4 taken along line 5-5.

Referring now to FIGS. 4 and 5, a primary absorbent article 22 is shown having a back waist region 48, a front waist region 45, and crotch region 64 bordered by a pair of leg cuffs 50 and 52. The front waist region 45 includes the portion of the primary absorbent article 22 that when worn, is positioned on the front of the wearer while the back waist region 48 includes the portion of the primary absorbent article 22 that when worn is positioned on the back of the wearer. The crotch region 64 of the primary absorbent article 22 includes the portion of the primary absorbent article 22 that when worn is positioned between the legs of the wearer and covers the lower torso of the wearer. Each of the pair of leg cuffs 50 and 52 can be elasticized, if desired, by incorporating one or more strands of elastic, 54 and 56 respectively. The primary absorbent article 22 also has a liquid-permeable body-side liner 58, a liquid-impermeable outercover 60, and an absorbent core 62 positioned therebetween. Desirably, the absorbent core 62 is completely enclosed between the body-side liner 58 and the outercover 60. The body-side liner 58 is designed to allow rapid intake of body fluid. The body-side liner 58 can be made from the same types of materials as were described above for the substrate 14 in the secondary article 10. The body-side liner 58 can be formed from a woven material, nonwoven material, finely perforated film, net material, and so forth. Suitable materials include bonded carded webs of polyester, polypropylene, polyethylene, nylon or other heat-bondable fibers. Other polyolefins, such as copolymers of polypropylene and polyethylene, and linear low-density polyethylene also work well.

The liquid-impermeable outercover 60 functions to prevent body fluid from passing therethrough. The liquid-impermeable outercover 60 can be made from a micro-embossed polymeric film, such as polyethylene or polypropylene, or it can be made from bicomponent films. A desired material is a polyethylene film having a thickness of less than about 0.08 mm. Composite materials formed from a polymer film and a nonwoven fabric material can also be used. The composite sheets may be formed by extrusion of the polymer film onto a web of spunbond material to form an integral sheet. This material is desirable because the outer fabric surface is not irritating to the skin of the wearer and has a cushioned feel.

The primary absorbent article 22 is depicted as having a pair of refastenable ears 66 and 68 and a fastening zone 65. The article 22 can be positioned around the torso of the wearer and the refastenable ears 66 and 68 fastened to the fastening zone 65. Such a design is advantageous in allowing for tightening or loosening the primary absorbent article 22 around the waist of the wearer.

It should be noted that the primary absorbent article 22 could be in the form of a pant product, brief product, undergarment, or any other absorbent article. The primary absorbent article 22 is desirably a disposable or limited use product that will be discarded after a single use. Furthermore, the primary absorbent article 22 can be an absorbent article that has a pocket or fold for containing a disposable insert or liner. Any and all such absorbent articles 22 are capable of being used in conjunction with the secondary article 10.

The secondary article 10 can be visualized as a secondary structure that is used to provide added features to the primary absorbent article 22. Since every consumer prefers different features, the secondary article 10 provides the consumer a vehicle to tailor the primary absorbent article 22 for the individual needs of the consumer.

In use, the secondary article 10 is secured to at least a portion of the body-side liner 58 in the crotch portion 64 of the primary absorbent article 22 before the primary absorbent article 22 is placed on the body of the wearer. For the embodiment depicted in FIGS. 1-3, the releasable peel strip 46 is removed from the secondary article 10, exposing the attachment means 44. The crotch portion 20 of secondary article 10 is then placed or aligned over at least a portion of the crotch portion 64 of the primary absorbent article 22. Alternatively, the secondary article 10 may be placed in the area of the primary absorbent article 22 where the skin is most in need of protection. The secondary article 10 is then pressed against the primary absorbent article 22 to secure the attachment means 44 thereto. Alternatively, the secondary article 10 may be secured to the primary absorbent article 22 by tucking one or more outer edges of the secondary article 10 inside a pocket or fold on the bodyfacing surface of the primary absorbent article 22. If present, the optional cover 24 is thereafter removed to expose the lotion 16. The primary absorbent article 22 can then be secured around the torso of the wearer. When the secondary article 10 is pressed against the skin of the wearer, the lotion 16 will transfer thereto.

While the invention has been described in detail with respect to specific embodiments thereof, and particularly by the example described herein, it will be apparent to those skilled in the art that various alterations, modifications and other changes may be made without departing from the spirit and scope of the present invention. It is therefore intended that all such modifications, alterations and other changes be encompassed by the following claims.

We claim:

1. A secondary article comprising:
a liquid-permeable fibrous substrate having a garment-facing surface and a body-facing surface;
an attachment means attached to the garment-facing surface, wherein the attachment means is adapted to be adhered to a primary absorbent article;
a semisolid lotion applied to the body-facing surface; and,
a cover releasably adhered directly to the lotion, wherein the cover has a Drape Stiffness bending length of between about 0.25 centimeters and about 12 centimeters.

2. The secondary article of claim 1 wherein the substrate comprises a spunbond material.

3. The secondary article of claim 1 wherein the lotion has a basis weight of greater than about 1 mg/cm$^2$.

4. the secondary article of claim 1 wherein the weight of the lotion is greater than the weight of the substrate.

5. The secondary article of claim 1 wherein the secondary article has a length of less than 600 millimeters.

6. The secondary article of claim 1 wherein the attachment means is selected from the group consisting of a garment adhesive, a hook material, and a roughened surface.

7. The secondary article of claim 1 wherein the attachment means further comprises a removable peel strip.

8. The secondary article of claim 1 wherein the lotion comprises an emollient and a wax.

9. The secondary article of claim 1 wherein the lotion is arranged in multiple stripes on the body-facing surface of the substrate.

10. The secondary article of claim 1 wherein the lotion is applied to at least about 5 percent of the body-facing surface of the substrate.

11. An absorbent system comprising:
a primary absorbent article; and,
the secondary article of claim 1 attached to the primary absorbent article.

12. The absorbent system of claim 11 wherein the secondary article is substantially the same shape as the primary absorbent article.

* * * * *